United States Patent [19]

Schroeder

[11] Patent Number: 5,035,689

[45] Date of Patent: Jul. 30, 1991

[54] LUER-LOC-TIPPED VIAL—SYRINGE COMBINATION

[76] Inventor: Thomas J. Schroeder, 2127 Tartan Rd., Anderson, Ind. 46012

[21] Appl. No.: 322,008

[22] Filed: Mar. 13, 1989

[51] Int. Cl.[5] .................... A61M 5/00

[52] U.S. Cl. .................... 604/234; 604/414; 141/2

[58] Field of Search ........ 604/195, 212, 218, 232-234, 604/236, 238, 405, 407, 414-411; 141/2, 27, 326, 357, 386

[56] References Cited

U.S. PATENT DOCUMENTS

| | | | |
|---|---|---|---|
| 1,960,858 | 5/1934 | Strauch | 604/212 |
| 2,724,384 | 11/1955 | Berthiot | 128/216 |
| 3,114,369 | 12/1963 | Hall | 128/216 |
| 3,578,037 | 5/1971 | Flynn | 141/2 |
| 3,610,297 | 10/1971 | Raaf et al. | 141/27 |
| 3,931,815 | 1/1976 | Takatsuki | 128/2 |
| 4,018,222 | 4/1977 | McAleer et al. | 128/216 |
| 4,022,206 | 5/1977 | Hillemen et al. | 128/216 |
| 4,046,145 | 9/1977 | Choksi et al. | 604/407 |
| 4,465,472 | 8/1984 | Urbaniak | 604/122 |
| 4,548,601 | 10/1985 | Larg | 604/204 |
| 4,568,346 | 2/1986 | van Dijk | 604/234 |
| 4,834,149 | 5/1989 | Fournier et al. | 604/411 |

*Primary Examiner*—Stephen C. Pellegrino
*Assistant Examiner*—Michael Rafa
*Attorney, Agent, or Firm*—Woodard, Emhardt, Naughton, Moriarty & McNett

[57] ABSTRACT

A vial of liquid removably attachable to a syringe. In one embodiment, a luer-loc-tip is integrally mounted to the vial which is removably mountable to a syringe for withdrawing liquid from the vial without the presence of a needle. In an alternate embodiment, the luer-loc flange is mountable to a conventional vial by means of clamps and enclosed by means of a sealing cap.

15 Claims, 2 Drawing Sheets

LUER-LOC-TIPPED VIAL—SYRINGE COMBINATION

BACKGROUND OF THE INVENTION

This invention is in the field of vials and syringes for use in injecting medicinal fluids. It is the normal practice to provide a single dose vial having a protective seal thereon which may be pierced by a hypodermic needle attached to a syringe for transferring the dose from the vial into the syringe. Alternatively, the needle may be affixed directly to the vial which may then be squeezed to inject the fluid into the patient from the vial.

Increased attention to possible contamination of the needle has required in many cases the replacement of the syringe needle once the dose is withdrawn from the vial and prior to injection of the fluid from the syringe. That is, the needle is removed from the syringe and a new needle installed thereby increasing the cost and time for each injection. I have therefore designed a vial having an outlet structured to attach directly to the syringe allowing the fluid to be withdrawn into the syringe without a needle extending between the vial and syringe. Once the fluid is withdrawn into the syringe, the vial may be removed and discarded and a needle affixed to the syringe outlet. The vial outlet takes advantage of the prior art luer-loc-tip of a needle. The need for a needle to withdraw medication is therefore eliminated. The lack of a needle also eliminates steps in the procedure that may lead to potential contamination. The luer-loc structure may be integral with the vial or may be provided by a flanged structure attachable to existing vials.

A number of U.S. Patents have been granted on the general subject matter; however, I am unaware of any patent or prior art directly showing or suggesting my combination. The U.S. Pat. No. 2,724,384 issued to Berthiot; U.S. Pat. No. 4,548,601 issued to Lary; and U.S. Pat. No. 4,018,222 issued to McAleer disclose single dose vials whose contents are injected directly into the patient. U.S. Pat. No. 3,114,369 issued to Hall discloses a thermo-plastic disposable vial, whereas U S. Pat. No. 4,465,472 issued to Urbaniak shows a syringe cartridge having a luer-loc-tipped cap U.S. Pat. No. 4,022,066 issued to Hilleman et al. shows a vial having a needle for puncturing the vial which is then used for direct injection. A similar approach is shown in U.S. Pat. No. 3,931,815 issued to Takatsuki.

SUMMARY OF THE INVENTION

One embodiment of the present invention is the combination of a vial of liquid including a hollow main body with an outlet, the vial further including an openable seal extending across the outlet to allow withdrawal of the liquid from the main body, the outlet including a first lock, and, a hollow casing including a plunger slidably mounted therein, the casing including an inlet and a second lock positioned adjacent the inlet, the inlet matable with the outlet with the second lock removable lockable with the first lock to secure the vial to the casing as the plunger is moved away from the inlet withdrawing the liquid from the vial into the casing.

Another embodiment of the present invention is a vial of liquid comprising a hollow main body with an outwardly extending first neck forming an outlet, the hollow main body further including an openable seal extending across the outlet to allow withdrawal of the liquid from the main body, the neck includes a mounting adapter thereon including a first lock with an outwardly extending flange formed exteriorly thereon.

It is an object of the present invention to provide a vial attachable directly to a syringe without a needle extending therebetween.

A further object of the present invention is to provide a luer-loc-tipped vial.

An additional object of the present invention is to provide a vial syringe combination whereby the liquid within the vial may be withdrawn directly into the syringe prior to the installation of a needle onto the syringe.

Related objects and advantages of the present invention will be apparent from the following description.

DESCRIPTION OF THE PREFERRED EMBODIMENTS

Figure 1:
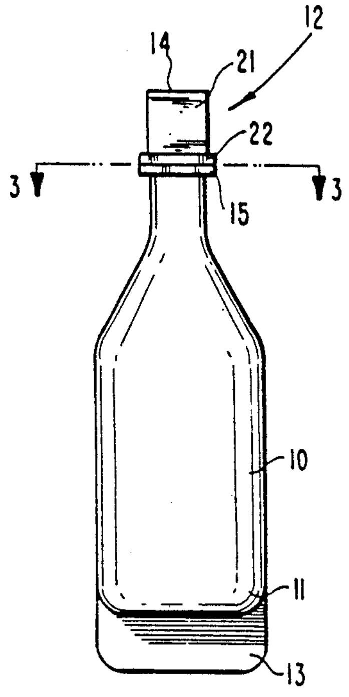
FIG. 1 is a side view of the preferred embodiment of the vial incorporating my new invention.
Figure 2:
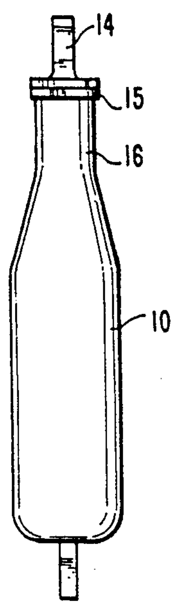
FIG. 2 is a right-hand side view of the vial of FIG. 1.
Figure 3:
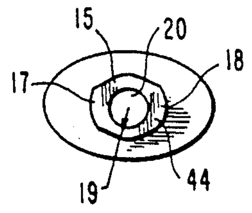
FIG. 3 is a cross-sectional view taken along line 3—3 of FIG. 1 and viewed in the direction of the arrows.
Figure 4:
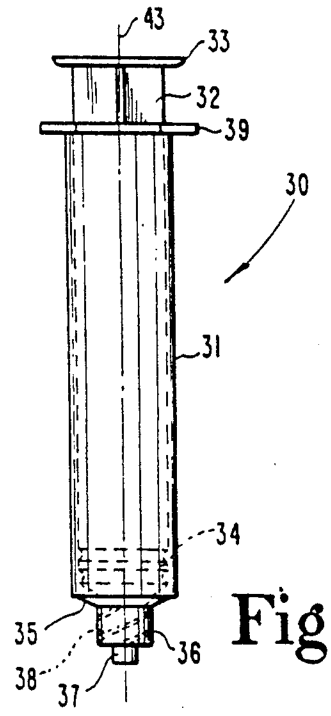
FIG. 4 is a side view of a syringe to be used with the vial of FIG. 1.
Figure 5:
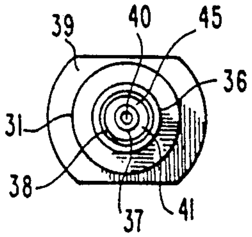
FIG. 5 is a bottom view of the syringe of FIG. 4.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIGS. 1-5, there is shown the preferred embodiment of my new invention. Vial 10 is a thermoplastic main body construction with a bottom end 11 and a top end 12. Initially, medicinal liquid is placed within the vial and the bottom end 11 is heat sealed along flange 13. The liquid may then be removed by breaking off the top cap 14 which is affixed to a luer-loc configured flange 15 integrally mounted atop neck 16 of the main body of the vial. Luer-loc flange 15 has a generally circular perimeter 19 with a pair of diagonally opposite ears 17 and 18 projecting radially outward. A passage 20 extends through flange 15 and neck 16 into the main body of the vial to allow the liquid therein to escape once cap 14 is removed.

Cap 14 has a handle 21 integrally joined to a cap flange 22 which is a mirror image of luer-loc flange 15. In other words, top flange 22 has a pair of ears extending outwardly atop ears 17 and 18. Flanges 15 and 22 have mutually facing surfaces which are secured together by adhesive or other suitable fastening means such as by heat sealing the flanges together. Flange 15, neck 16 and the main body of vial 10 are integrally connected together with flange 22 being integrally connected to handle 21. In the event flanges 15 and 22 are heat sealed together, then the cap as well as the main body of the vial provide a unitary integral construction.

Syringe 30 includes a hollow casing 31 having a plunger 32 slidably mounted therein. The plunger has a top enlarged end 33 and a bottom sealing end 34 movable between the bottom end 35 and enlarged flanged end 39 of casing 31. Bottom end 34 has a plurality of O-rings thereon for sealingly engaging the cylindrical inner surface of casing 31. A hollow sleeve 36 is integrally attached to the bottom end 35 of the casing and is concentric with, but spaced apart from a tube 37 likewise integrally mounted to bottom end 35. Tube 37 has a passage 40 extending into the hollow interior of casing 31. A plurality of threads 38 are formed in the inner surface of sleeve 36 facing the outer surface of tube 37 to releasably lock onto the luer-loc-tipped flange 15 of vial 10.

Figure 6:
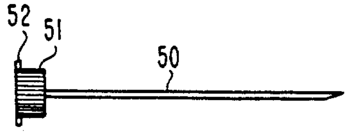
FIG. 6 is a side of a conventional luer-loc-tipped hypodermic needle.
Figure 8:
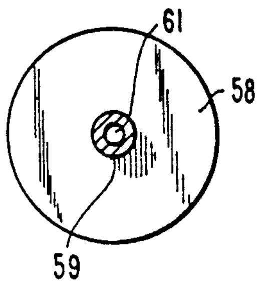
FIG. 8 is a cross-sectional view taken along the line and viewed in the direction of arrows 8—8 of FIG. 7.
Figure 9:
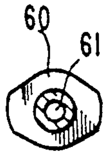
FIG. 9 is a cross-sectional view taken along the line and viewed in th direction of arrow 9—9 of FIG. 7.

Once vial 10 is filled with medicinal liquid at the place of manufacture, the user may break off handle 14 by separating with force flanges 22 and 15. This may be done by rotating handle 21 relative to the longitudinal axis of the main body of vial 10 until the fastening means securing flanges 15 and 22 is ruptured. Once the handle is separated from the vial, flange 15 may be inserted in the direction of the longitudinal axis 43 of casing 31 into the annular cavitY 41 formed between tube 37 and sleeve 36. Syringe 30 and annular cavity 41 are shown reduced in size in the drawing relative to flange 15, it being understood that in actual size, the syringe and cavity would be larger to enable flange 15 to fit into cavity 41. Tube 37 will thereby enter into passage 20 with ears 17 and 18 then extending into the grooves formed between threads 38. The vial is then rotated about the longitudinal axis 43 of casing 31 advancing flange 15 along threads 38 until the top surface 44 of flange 15 contacts the downward facing surface 45 within annular cavity 41. The plunger may then be pulled upwardly relative to casing 31 withdrawing the liquid from vial 10 into the interior cavity of casing 31 existing between the bottom end 34 of the plunger and the bottom end 35 of the casing. Once the desired amount of liquid has been withdrawn into the casing, the vial is then rotated in an opposite direction relative the casing until the vial is completely disengaged from the casing. The vial is then discarded and a conventional luer-loc-tipped hypodermic needle 50 is mounted to the syringe by extending the ears 52 (FIG. 6) of end 51 of needle 50 into annular cavity 41 and between threads 38. The needle is rotated relative to casing 31 until the ears are in contact with surface 45. The plunger may then be moved downwardly or depressed relative to the casing injecting the liquid within the casing via needle 50 into the patient.

Figure 7:
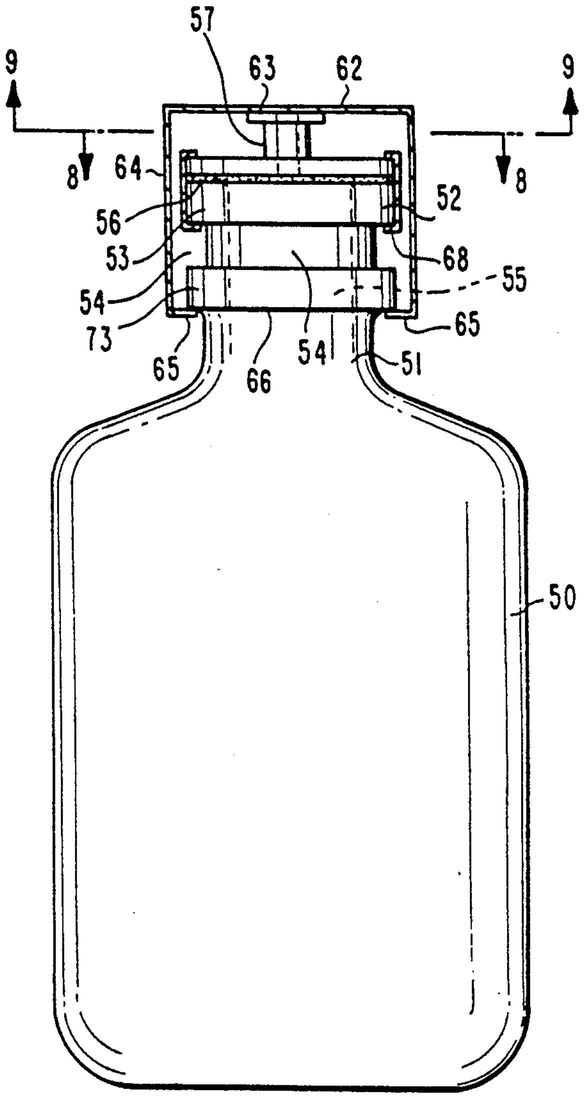
FIG. 7 is a side view of an alternate embodiment of the vial of FIG. 1.

The alternate embodiment of my invention is shown in FIG. 7 and is identical to the preferred embodiment with the exception that the luer-loc configured flange is mounted directly to a conventional vial and with the further exception that seals are provided in lieu of the handle previously described. Vial 50 has a hollow interior containing the medicinal liquid to be dispensed. A neck 51 is integrally attached to the main body of the vial and has a grooved top end 52 forming a pair of rings 53 and 73 separated by cylindrical groove 54. The hollow main body of vial 50 opens outwardly through a passage 55 extending through rings 53 and 73 providing an outlet for the vial. Passage 55 is sealingly closed by a conventional disk-shaped gasket 56 positioned between ring 53 and mounting adapter 57. Adapter 57 has a disk-shaped base 58 integrally attached to an upwardly extending neck 59 in turn attached to luer-loc shaped top flange 60. Passage 61 extends through base 58, neck 59 and flange 60 allowing liquid within passage 55 to flow outwardly once outer seal 62 is removed. Passage 61 extends through gasket 56 into passage 55. Flange 60 is shaped identically to flange 15 for the embodiment of FIG. 1 and has an outer perimeter with two ears which extend into annular cavity 41 of sleeve 36 (FIG. 4) when the adapter is mounted to the casing for withdrawal of the liquid within vial 50.

Outer seal 62 is shown in cross-section to illustrate the mounting flange and the top of vial 50. Outer seal 62 includes a disk-shaped top wall 63 integrally joined to a depending skirt 64 which completely surrounds the mounting adapter 57 and the top of the vial. The skirt has an inwardly turned bottom edge 65 which abuts against the lower ledge surface 66 of ring 73. Outer seal 62 may be produced from a suitable material such as plastic and may simply be removed by prying the seal from the vial. The downwardly facing surface of top wall 63 extends across the upwardly facing surface of flange 60 to sealingly close passage 61.

Mounting adapter 57 is held securely against gasket 56 which in turn is held securely against the top surface of ring 52 by means of a plurality of C-shaped clamps 68. Each clamp 68 includes a top and bottom inwardly facing edge portion which extends respectively against the upwardly facing surface of base 58 and the downwardly facing ledge surface of ring 53. The inner seals 68 are designed to fixedly secure mounting adapter 57 to the vial to prevent accidental disengagement thereof.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. The combination of:

a vial of liquid including a hollow main body with an outlet, said vial further including openable sealing means extending across said outlet to allow withdrawal of said liquid from said main body, said outlet including first locking means having a luer-loc flange integrally formed thereon; and, a hollow casing including a plunger slidably mounted therein, said casing including an inlet and second locking means positioned adjacent said inlet and non-removable therefrom, said inlet connectable with said outlet with said second locking means removable lockable directly to said luer-loc flange of said first locking means to secure said vial to said casing as said plunger is moved away from said inlet withdrawing said liquid from said vial into said casing, said casing further including a needle mountable to said inlet once said vial is removed therefrom.

2. The combination of claim 1 wherein:

said hollow main body includes an outwardly extending first neck forming said outlet and said hollow casing includes a outwardly extending tube slidably connectable with said neck, said first locking means and said second locking means includes an outwardly extending flange on said neck and a groove positioned on said tube which are matable together.

3. The combination of claim 2 wherein:

said hollow casing includes a sleeve concentric with but outwardly of said tube with said tube extendable into said neck which is extendable between said tube and said sleeve.

4. The combination of claim 3 wherein:

said first locking means is formed exteriorly on said neck and said second locking means is formed interiorly on said sleeve.

5. The combination of claim 4 wherein:

said first locking means includes a pair of diametrically opposed and outwardly extending flanges oriented perpendicularly to said neck, said second locking means includes a spiral groove on said sleeve opening toward said tube which slidably receives said flanges to removably lock said vial to said casing.

6. The combination of claim 5 wherein said main body of said vial and said flanges are integrally secured together and form a unitary and squeezable plastic construction sized to hold a single dose of said liquid.

7. The combination of claim 5 wherein:

said openable sealing means includes a cap removably affixed atop and to said first neck, said cap includes a handle which may grasped to twist off said cap from said first neck exposing said outlet.

8. The combination of claim 5 wherein:

said hollow main body includes a second neck with a passage extending therethrough into said vial, said first neck includes a base seated upon said second neck with said outlet aligned with said passage; and further comprising:

an inner seal securing said base to said second neck.

9. The combination of claim 8 wherein:

said openable sealing means is mounted and affixed to said second neck and extends upwardly around said second neck and said first neck enclosing both said first neck and said second neck while sealing said outlet.

10. A vial of liquid comprising:

a hollow main body with an outwardly extending first neck forming an outlet, said hollow main body further including openable sealing means extending across said outlet to allow withdrawal of said liquid from said main body, said neck includes mounting adapter means thereon including first locking means with an outwardly extending flange formed exteriorly thereon, said mounting adapter means further including a base and a luer-loc flange joined together by said neck, said first locking means located on said luer-loc flange and includes a pair of diametrically opposed and outwardly extending flanges oriented perpendicularly to said neck, said hollow main body further including a second neck with a passage extending therethrough into said hollow main body, said base seated upon said second neck with said outlet aligned with said passage, and further comprising an inner seal securing said base to said second neck.

11. The vial of claim 10 wherein:

said openable sealing means is mounted and affixed to said second neck and extends upwardly around said second neck and said first neck enclosing both said first neck and said second neck while sealing said outlet.

12. A syringe-vial device comprising:

a vial of liquid with said vial having a luer-loc flange integrally formed thereon:

a cylindrical shaped casing with a first end having a tube forming a passage into said casing and further having a sleeve thereon to receive said vial with said sleeve concentrically located outwardly of said tube, said first end of said casing connected to a syringe needle once said vial is removed therefrom; and, a plunger slidable mounted in said casing to withdraw liquid from said vial through said passage into said casing.

13. The device of claim 14 wherein:

said sleeve includes an inner surface facing said tube with a thread formed thereon defining a groove to receive said vial.

14. The device of claim 15 wherein:

said casing includes a stop surface, said tube extends outwardly from said stop surface a distance greater than said sleeve.

15. The device of claim 16 wherein:

said tube and said sleeve define a annular cavity which opens outwardly from said stop surface against which said vial is held securely against by said thread.

* * * * *

UNITED STATES PATENT AND TRADEMARK OFFICE
CERTIFICATE OF CORRECTION

PATENT NO. : 5,035,689

DATED : July 30, 1991

INVENTOR(S) : Thomas J. Schroeder

It is certified that error appears in the above-identified patent and that said Letters Patent is hereby corrected as shown below:

In Column 1, line 45, please change "cap U.S." to --cap. U.S.--.

In Column 6, line 37, please change "claim 14" to --claim 12--.

In Column 6, line 41, please change "claim 15" to --claim 13--.

In Column 6, line 45, please change "claim 16" to --claim 14--.

Signed and Sealed this

Fifth Day of January, 1993

*Attest:*

DOUGLAS B. COMER

*Attesting Officer*

*Acting Commissioner of Patents and Trademarks*